United States Patent
Das et al.

(10) Patent No.: US 9,649,083 B2
(45) Date of Patent: May 16, 2017

(54) SYSTEM AND METHOD FOR RECALIBRATING A MONOCHROMATIC IMAGE

(71) Applicant: General Electric Company, Schenectady, NY (US)

(72) Inventors: Bipul Das, Karnataka (IN); Ajay Narayanan, Karnataka (IN); Pratik Shah, Karnataka (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/964,052

(22) Filed: Dec. 9, 2015

(65) Prior Publication Data

US 2016/0171694 A1 Jun. 16, 2016

(30) Foreign Application Priority Data

Dec. 10, 2014 (IN) .......................... 6233/CHE/2014

(51) Int. Cl.
G06K 9/00 (2006.01)
A61B 6/00 (2006.01)
G06T 11/00 (2006.01)
G06T 5/00 (2006.01)
G06T 7/11 (2017.01)
A61B 6/03 (2006.01)
G06T 7/136 (2017.01)

(52) U.S. Cl.
CPC .............. *A61B 6/505* (2013.01); *A61B 6/501* (2013.01); *A61B 6/5217* (2013.01); *G06T 5/009* (2013.01); *G06T 7/11* (2017.01); *G06T 11/008* (2013.01); *A61B 6/032* (2013.01); *G06T 7/136* (2017.01); *G06T 2207/10081* (2013.01); *G06T 2207/30008* (2013.01)

(58) Field of Classification Search
None
See application file for complete search history.

(56) References Cited

U.S. PATENT DOCUMENTS 6,115,487 A 9/2000 Toth et al.
7,856,134 B2 * 12/2010 Ruhrnschopf ......... A61B 6/032
382/128

(Continued)

OTHER PUBLICATIONS

Fan et al., "A Scatter Artifact Reduction Technique in Dual-Energy Computed Tomography Systems", Procceedings of SPIE 7961, Medical Imaging 2011: Physics of Medical Imaging,79613B, vol. 7961, 2011.

*Primary Examiner* — Weiwen Yang

(57) ABSTRACT

A method includes receiving a monochromatic image comprising a head of a subject from a Computed Tomography (CT) scanner and detecting a petrous bone of the head in the monochromatic image. The method further includes determining a linear attenuation coefficient of at least one petrous voxel representing the petrous bone and calculating a mass attenuation coefficient of the petrous voxel based on the linear attenuation coefficient and a density of the petrous bone. The method also includes computing a monochromatic energy level of the monochromatic image based on the mass attenuation coefficient of the petrous voxel and recalibrating the monochromatic image corresponding to the computed monochromatic energy level to the desired monochromatic energy level.

10 Claims, 6 Drawing Sheets

(56) References Cited

U.S. PATENT DOCUMENTS

| | | |
|---|---|---|
| 2003/0031299 A1 | 2/2003 | Ohishi |
| 2003/0053597 A1 | 3/2003 | Flohr et al. |
| 2005/0002484 A1 | 1/2005 | Wu et al. |
| 2006/0159223 A1 | 7/2006 | Wu et al. |
| 2008/0192898 A1 | 8/2008 | Van Metter et al. |
| 2008/0260106 A1 | 10/2008 | Davilla |
| 2009/0161814 A1 | 6/2009 | Wu et al. |
| 2012/0069952 A1 | 3/2012 | Wu et al. |
| 2013/0331686 A1* | 12/2013 | Freysinger ............. A61B 34/20 600/417 |
| 2014/0140478 A1* | 5/2014 | Hsieh ....................... A61B 6/06 378/62 |

* cited by examiner

SYSTEM AND METHOD FOR RECALIBRATING A MONOCHROMATIC IMAGE

BACKGROUND

The technology disclosed herein generally relates to Computed Tomography (CT) imaging systems. More specifically, the subject matter relates to systems and methods to recalibrate a monochromatic image received from a CT imaging system based on a petrous bone.

CT is a technology that uses X-rays to produce tomographic images (i.e., virtual slices) of a subject (e.g., a head/head-neck region of a human patient). The tomographic slices are then used to generate a three-dimensional (3D) CT image of the subject. Currently, multi-energy spectral CT systems have been developed that can determine densities of different materials in a subject and generate CT images acquired at multiple monochromatic X-ray energy levels. Typically, the multi-energy spectral CT systems include one or more X-ray sources for projecting one or more X-ray beams at a plurality of energy levels towards the subject. Although, an X-ray source projects one or more X-ray beams at a particular energy (e.g., 80 peak kilovoltages, 140 peak kilovoltages, and the like), the respective X-ray emissions at a given energy are actually along an energy continuum or spectrum and, therefore, constitute a polychromatic emission centered at, or having a peak strength at, the desired energy level. The multi-energy spectral CT systems further include one or more X-ray detection units that receive the one or more X-ray beams attenuated by the subject and generate polychromatic images of the subject. The X-ray detection units further generate monochromatic images of the subject that simulate how the subject would appear in an image, if the image were obtained based on a true monochromatic X-ray source, i.e., an X-ray source that projects an X-ray beam of a single energy level expressed in Kilo electron Voltage.

However, such multi-energy spectral CT scanners may generate erroneous monochromatic images due to multiple sources of variations, leading to incorrect measurements of image Hounsfield Units and density values. The multiple sources of variations include, for example, variations caused by the operation and the location of the X-ray sources, variations due to erroneous inputs from the administrators of the X-ray sources, variations in material densities across different subjects, and the like. Thus, there is a need for a system and method for recalibrating the monochromatic images.

BRIEF DESCRIPTION

In accordance with one aspect of the present technique, a method includes receiving a monochromatic image comprising a head of a subject from a Computed Tomography (CT) scanner and detecting a petrous bone of the head in the monochromatic image. The method further includes determining a linear attenuation coefficient of at least one petrous voxel representing the petrous bone and calculating a mass attenuation coefficient of the petrous voxel based on the linear attenuation coefficient and a density of the petrous bone. The method also includes computing a monochromatic energy level of the monochromatic image based on the mass attenuation coefficient of the petrous voxel and recalibrating the monochromatic image corresponding to the computed monochromatic energy level to the desired monochromatic energy level.

In accordance with one aspect of the present system, a system includes a petrous detector configured to receive a monochromatic image comprising a head of a subject from a CT scanner and detect a petrous bone of the head in the monochromatic image. The system further includes an attenuation unit configured to determine a linear attenuation coefficient of at least one petrous voxel representing the petrous bone, calculate a mass attenuation coefficient of the petrous voxel based on the linear attenuation coefficient and a density of the petrous bone and compute a monochromatic energy level of the monochromatic image based on the mass attenuation coefficient of the petrous voxel. The system also includes a recalibration module configured to recalibrate the monochromatic image corresponding to the computed monochromatic energy level to the desired monochromatic energy level.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

In the following specification and the claims, reference will be made to a number of terms, which shall be defined to have the following meanings.

The singular forms "a", "an", and "the" include plural references unless the context clearly dictates otherwise.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

As used herein, the terms "software" and "firmware" are interchangeable, and include any computer program stored in memory for execution by devices that include, without limitation, mobile devices, clusters, personal computers, workstations, clients, and servers.

As used herein, the term "computer" and related terms, e.g., "computing device", are not limited to integrated circuits referred to in the art as a computer, but broadly refers to at least one microcontroller, microcomputer, programmable logic controller (PLC), application specific integrated circuit, and other programmable circuits, and these terms are used interchangeably herein.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Figure 1:
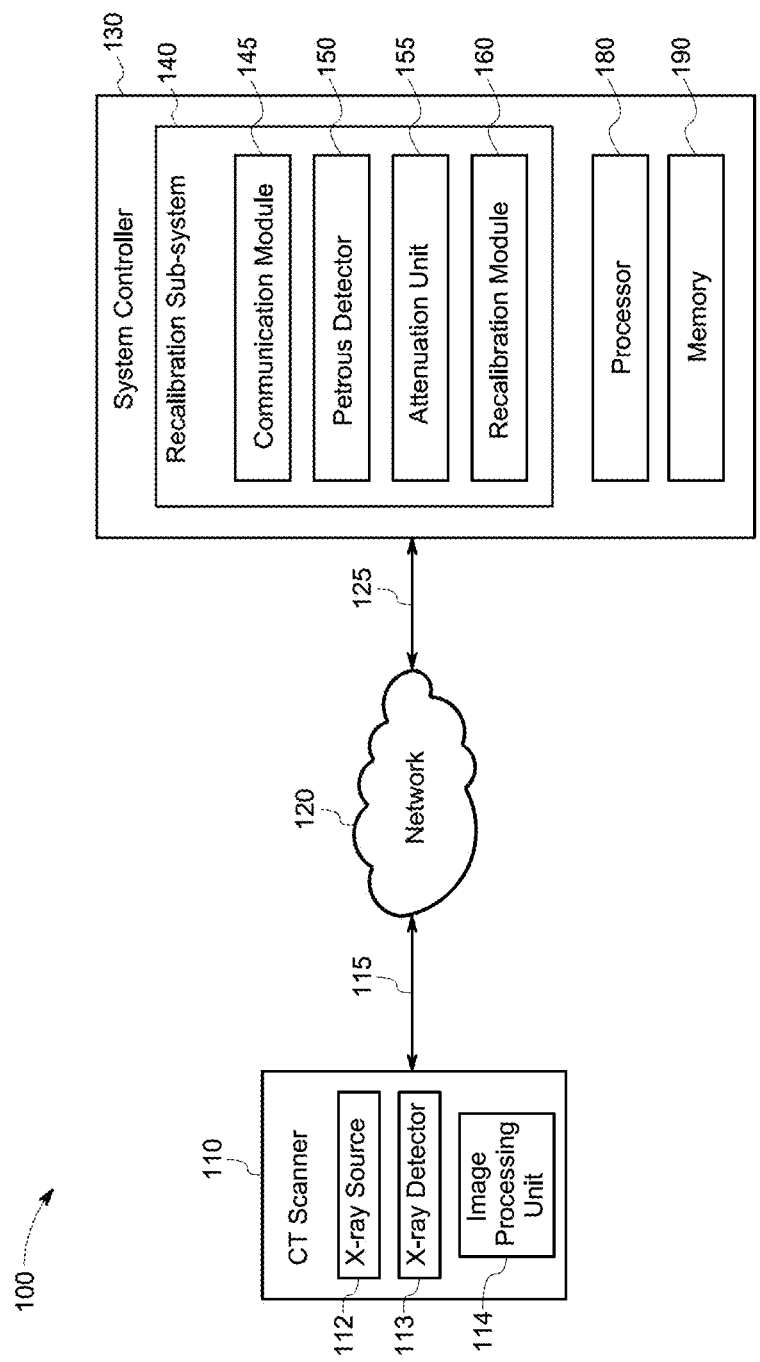
FIG. 1 is a block diagram illustrating a system for recalibrating a monochromatic image according to one embodiment.

A system and method for recalibrating a monochromatic image is described herein. FIG. 1 illustrates a block diagram of a system 100 configured to recalibrate a monochromatic image according to one embodiment. The system 100 includes a CT scanner 110 and a system controller 130 that are communicatively coupled via a network 120. Although the CT scanner 110 and the system controller 130 are communicatively coupled via the network 120 according to FIG. 1, the system controller 130 may be included within the CT scanner 110.

The network 120 may be a wired or wireless type, and may have any number of configurations such as a star configuration, a token ring configuration, or other known configurations. Furthermore, the network 120 may include a local area network (LAN), a wide area network (WAN) (e.g., the internet), and/or any other interconnected data path across which multiple devices may communicate. In one embodiment, the network 120 may be a peer-to-peer network. The network 120 may also be coupled to or include portions of a telecommunication network for sending data in a variety of different communication protocols. In one embodiment, the network 120 may include Bluetooth communication networks or a cellular communications network for sending and receiving data such as via a short messaging service (SMS), a multimedia messaging service (MMS), a hypertext transfer protocol (HTTP), a direct data connection, a wireless application protocol (WAP), an email, or the like.

The CT scanner 110 may be any type of scanner that is configured to project one or more X-ray beams towards a subject (e.g., a human patient) and generate one or more three-dimensional (3D) CT images of the subject by receiving and processing the one or more X-ray beams that have been attenuated by the subject. In the illustrated embodiment, the CT scanner 110 is a multi-energy spectral CT scanner 110 (e.g., dual x-ray source and detector, a single x-ray source with an energy discriminative detector, a single x-ray source and detector with multiple acquisitions at different peak kilovoltages (kVp) or interleaved with fast kVp switching capability, and the like) that is configured to generate CT images comprising a head or a head/neck region of a subject. The CT scanner 110 is communicatively coupled to the network 120 via signal line 115. The signal line 115 is provided for illustrative purposes and represents the CT scanner 110 communicating by wires or wirelessly over the network 120.

The CT scanner 110 comprises at least one X-ray source 112 configured to project an X-ray beam at a plurality of energies towards a subject. For example, the X-ray source 112 may be configured to switch between projecting a relatively low energy polychromatic X-ray emission spectra (e.g., at about 80 kVp) and a relatively high energy polychromatic X-ray emission spectra (e.g., at about 140 kVp). Although, the X-ray source 112 is configured to project X-rays at a particular energy (e.g., 80 kvP, 140 kVp, and the like), the respective X-ray emissions at a given energy are actually along an energy continuum or spectrum and, therefore, constitute a polychromatic emission centered at, or having a peak strength at, the desired energy level. As will be appreciated, the X-ray source 112 may also be configured to project X-rays at more than two different energies. Similarly, the X-ray source 112 may be configured to project at polychromatic spectra localized around energy levels (i.e., kVp ranges) other than those listed herein.

The CT scanner 110 further comprises at least one X-ray detector 113 configured to receive the X-ray beam attenuated by the subject and generate electrical signals representing the intensity of the incident X-ray beam. The X-ray detector 113 sends the electrical signals to the image processing unit 114. The image processing unit 114 processes the electrical signals to generate a plurality of polychromatic images that represent the subject based on the attenuation information of the X-ray beam having energies across the entire source spectrum rather than a single energy level. For example, the image processing unit 114 is configured to generate a low energy polychromatic image corresponding to the low energy polychromatic X-ray emission spectra (e.g., at about 70 kVp) and a high energy polychromatic image corresponding to the high energy polychromatic X-ray emission spectra (e.g., at about 140 kVp).

The image processing unit 114 is further configured to generate one or more simulated monochromatic images based on at least two polychromatic images. A monochromatic image is intended to simulate how the subject would appear in an image, if the image were obtained based on a true monochromatic X-ray source, i.e., an X-ray source that projects an X-ray beam of a single energy level expressed in Kilo electron Volts (KeV). In one embodiment, the image processing unit 114 generates the one or more monochromatic images using a projection-based reconstruction process based on attenuation curves of two or more compositions/materials of interest along the polychromatic spectra corresponding to the polychromatic images. In such an embodiment, the image processing unit 114 generates a first and a second material decomposition (MD) image and corresponding noise maps by performing a polynomial transformation of, for example, the 80 kVp and 140 kVp polychromatic images into material densities of material pairs of interest. For example, the image processing unit 114, generates a water image, an iodine image (i.e., the first and the second MD images), and corresponding noise maps. The image processing unit 114 then generates one or more monochromatic images based on a linearly weighted combination of the first and the second MD images and the corresponding noise maps. The image processing unit 114 is further configured to send the one or more monochromatic images, the MD images, and the noise maps to the system controller 130 via the network 120.

The system controller 130 may be any type of device configured to recalibrate one or more monochromatic images based on a petrous bone of a subject. The system controller 130 is communicatively coupled to the network 120 via signal line 125. The signal line 125 is provided for illustrative purposes and represents the system controller 130 communicating by wires or wirelessly over the network 120. Although one system controller 130 is shown in FIG. 1, a plurality of system controllers 130 may be coupled to the network 120. Additionally, although the system controller 130 is communicatively coupled to the CT scanner 110 via the network 120, the processing of the system controller 130 may be performed within the CT scanner 110. In the illustrated system 100, the system controller 130 includes a recalibration sub-system 140, a processor 180, and a memory 190. The recalibration sub-system 140 includes a communication unit 145, a petrous detector 150, an attenuation unit 155, and a recalibration module 160. The sub-units of the recalibration sub-system 140, the processor 180, and the memory 190 are coupled to a bus (not shown) for communication with each other. The one or more sub-units of the reference plane generator 140 include codes and routines that may be implemented as software, hardware, or a combination of software and hardware.

The processor 180 may include at least one arithmetic logic unit, a microprocessor, a general purpose controller or other processor arrays to perform computations, and/or retrieve data stored in the memory 190. In one embodiment, the processor 180 may be a multiple core processor. The processor 180 processes data signals and may include various computing architectures including a complex instruction set computer (CISC) architecture, a reduced instruction set computer (RISC) architecture, or an architecture implementing a combination of instruction sets. In one embodiment, the processing capability of the processor 180 may be limited to supporting the retrieval of data and transmission of data. In another embodiment, the processing capability of the processor 180 may also perform more complex tasks, including various types of feature extraction, modulating, encoding, multiplexing, and the like. Other type of processors, operating systems, and physical configurations are also envisioned.

The memory 190 may be a non-transitory storage medium. For example, the memory 190 may be a dynamic random access memory (DRAM) device, a static random access memory (SRAM) device, a flash memory or other memory devices. The memory 190 may also include a non-volatile memory or similar permanent storage device, and media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices.

The memory 190 stores data that is required for the recalibration sub-system 140 to perform associated functions. In one embodiment, the memory 190 stores the sub-units (e.g., the communication unit 145, the recalibration module 160, and the like) of the recalibration sub-system 140. In another embodiment, the memory 190 stores a density of the petrous bone, a petrous threshold value that is defined by, for example, an operator of the system controller 130. The petrous threshold value is described below in further detail with reference to the petrous detector 150.

The communication unit 145 includes codes and routines configured to handle communications between the CT scanner 110 and the sub-units of the recalibration sub-system 140. In one embodiment, the communication unit 145 includes a set of instructions executable by the processor 180 to provide the functionality for handling communications between the CT scanner 110 and the sub-units of the recalibration sub-system 140. In another embodiment, the communication unit 145 is stored in the memory 190 and is accessible and executable by the processor 180. In either embodiment, the communication unit 145 is adapted for communication and cooperation with the processor 180 and other sub-units of the recalibration sub-system 140.

In one embodiment, the communication unit 145 receives one or more monochromatic images comprising a head or a head/neck region of a subject, MD images, and corresponding noise maps from the CT scanner 110. In such an embodiment, the communication unit 145 sends the one or more monochromatic images to the petrous detector 150 and the MD images and the noise maps to the recalibration module 160. In another embodiment, the communication unit 145 receives a recalibrated monochromatic image from the recalibration module 160. In such an embodiment, the communication unit 145 sends the recalibrated monochromatic image to, for example, a display device (not shown), an operator of the system controller 130, and the like.

The petrous detector 150 includes codes and routines configured to determine a petrous bone of the head in a monochromatic image. Typically, a head of a human subject comprises two petrous bones. In one embodiment, the petrous detector 150 includes a set of instructions executable by the processor 180 to provide the functionality for determining a petrous bone of the head in the monochromatic image. In another embodiment, the petrous detector 150 is stored in the memory 190 and is accessible and executable by the processor 180. In either embodiment, the petrous detector 150 is adapted for communication and cooperation with the processor 180 and other sub-units of the recalibration sub-system 140.

The petrous detector 150 receives the monochromatic image comprising a head of a subject from the communication unit 145. In one embodiment, the petrous detector 150 determines whether the attenuation/intensity value of each voxel in the monochromatic image exceeds a petrous threshold value. The petrous threshold value is defined by, for example, an operator of the system controller 130 based on attenuation values corresponding to petrous bones in previously generated clinical data. The petrous detector 150 detects one or more voxels in the monochromatic image as the petrous bones of the head in response to determining that the attenuation values of the one or more voxels exceed the petrous threshold value. For example, the petrous detector 150 labels/classifies two voxels with attenuation values 0.8 and 0.82 units as a petrous bone, since they exceed the petrous threshold value of 0.75 units. In such an example, the petrous detector 150 fails to label a voxel with an attenuation value of 0.5 units as it is lesser than the petrous threshold value of 0.75 units.

In a further embodiment, the petrous detector 150 determines the petrous bones in the monochromatic image based on the positional information (e.g., x,y, and z co-ordinates) of the one or more voxels in the monochromatic image. This is beneficial as the petrous detector 150 avoids classifying voxels that are located, for example, near the neck or mouth regions in the monochromatic image as a petrous bone. In the above example, the received monochromatic image includes a voxel with an attenuation value of 0.78 units that corresponds to a dental implant of the subject. Although, the attenuation value of the voxel exceeds the petrous threshold value, the petrous detector 150 fails to classify it as a petrous bone as the positional information of the voxels indicates that the voxel represents the mouth region of the head. The petrous detector 150 is also configured to send information (e.g., location) corresponding to the one or more voxels representing the petrous bones in the monochromatic image to the attenuation unit 155.

Figure 2:
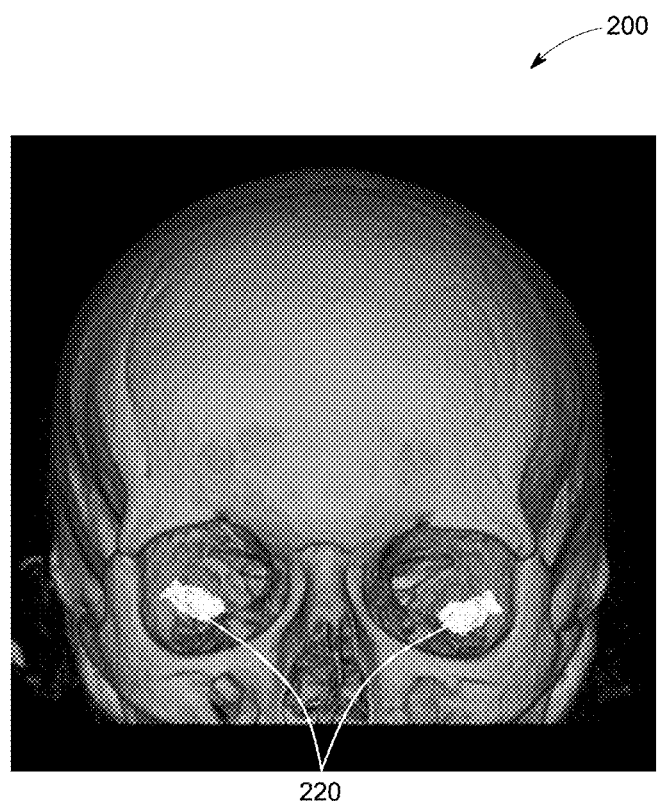
FIG. 2 is a computed tomography image including petrous bones of a head according to one embodiment.

Referring now to FIG. 2, a CT image 200 including a head of a subject is illustrated according to one embodiment. The CT image 200 illustrates the petrous bones 220 detected by the petrous detector.

Referring back to FIG. 1, an attenuation unit 155 includes codes and routines configured to determine a linear attenuation coefficient and a mass attenuation coefficient of one or more petrous voxels. The petrous voxel is a voxel representing the petrous bone in the monochromatic image. In one embodiment, the attenuation unit 155 includes a set of instructions executable by the processor 180 to provide the functionality for determining the linear attenuation coefficient and the mass attenuation coefficient of the one or more petrous voxels. In another embodiment, the attenuation unit 155 is stored in the memory 190 and is accessible and executable by the processor 180. In either embodiment, the attenuation unit 155 is adapted for communication and cooperation with the processor 180 and other sub-units of the recalibration sub-system 140.

The attenuation unit 155 receives information regarding the one or more petrous voxels from the petrous detector 150. The attenuation unit 155 is configured to determine a linear attenuation coefficient of a petrous voxel based on the intensity level i.e., Hounsfield Unit (HU) of the petrous voxel in the monochromatic image. The attenuation unit 155 is further configured to calculate the mass attenuation coefficient of the petrous voxel based on the linear attenuation coefficient of the petrous voxel and the density of the petrous bone. In one embodiment, the attenuation unit 155 calculates the mass attenuation coefficient of the petrous voxel based on the equation:

$$\mu(E) = K(E)/(\rho * \alpha) \quad (1)$$

Where, $\mu$ is the mass attenuation coefficient of the petrous voxel; E is the monochromatic energy level; K is the linear attenuation coefficient of the petrous voxel; $\alpha$ is number of materials represented in the petrous voxel. In this embodiment, $\alpha$ equals one, since the petrous voxel represents the petrous bone comprising a single material, i.e., calcium hydroxyapatite; and $\rho$ is the density of the petrous bone. In this embodiment, $\rho$ is equivalent to 1.98 units and is retrieved by the attenuation unit from the memory 190.

Figure 3:
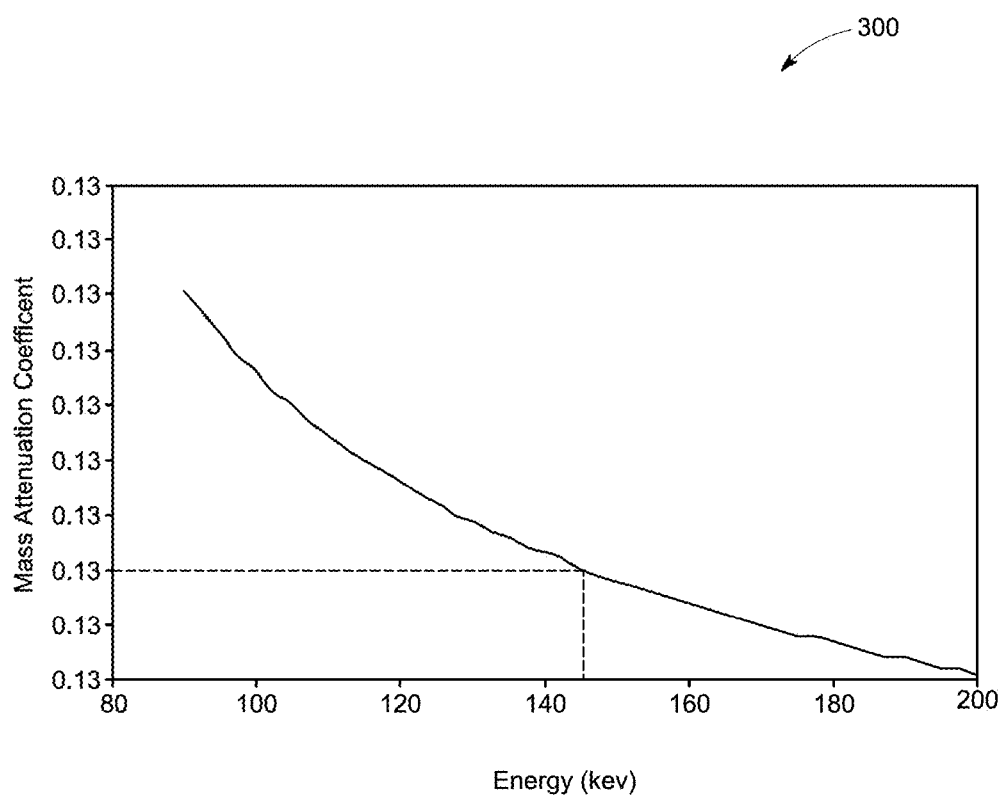
FIG. 3 is a graphical representation illustrating a mass attenuation coefficient versus monochromatic energy level graph according to one embodiment.

The attenuation unit 155 further computes the monochromatic energy level (E) of the received monochromatic image based on the mass attenuation coefficient. Referring now to FIG. 3, a standard mass attenuation coefficient versus monochromatic energy level graph 300 is illustrated. The x-axis represents the monochromatic energy level in keV and the y-axis represents the mass attenuation coefficient of the petrous bone in meter squared per kilogram. In the illustrated example, since the calculated mass attenuation coefficient is 0.15 meter squared per kilogram, the attenuation unit computes the monochromatic energy level of the monochromatic image as 145 keV. Referring back to FIG. 1, the attenuation unit 155 is further configured to send the computed monochromatic energy level and the monochromatic image to the recalibration module 160.

The recalibration module 160 includes codes and routines configured to recalibrate a monochromatic image. In one embodiment, the recalibration module 160 includes a set of instructions executable by the processor 180 to provide the functionality for recalibrating the monochromatic image. In another embodiment, the recalibration module 160 is stored in the memory 190 and is accessible and executable by the processor 180. In either embodiment, the recalibration module 160 is adapted for communication and cooperation with the processor 180 and other sub-units of the recalibration sub-system 140.

The recalibration module 160 receives the monochromatic image and the computed monochromatic energy level from the attenuation unit 155. The recalibration module 160 determines whether the computed monochromatic energy level is different from a desired monochromatic energy level. The recalibration module 160 receives the desired monochromatic energy level from the memory 190 or as user input from, for example, an administrator of the system controller 130. The recalibration module 160 recalibrates the received monochromatic energy to the desired monochromatic energy level in response to determining that the computed monochromatic energy level is different from the desired monochromatic energy level.

Figure 4:
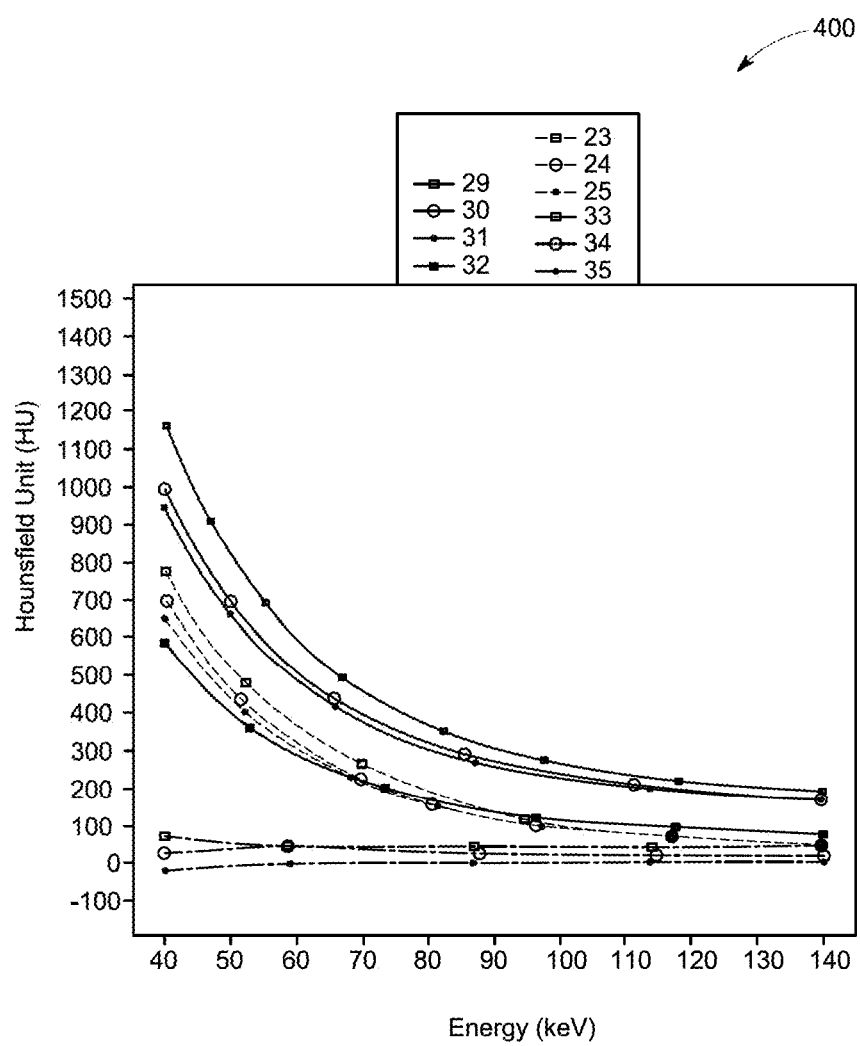
FIG. 4 is a graphical representation illustrating a spectral Hounsfield Unit curve according to one embodiment.

In one embodiment, the recalibration module 160 recalibrates the monochromatic image based on a spectral HU curve. In another embodiment, the recalibration module recalibrates the monochromatic image based on a spectral attenuation curve. Referring now to FIG. 4, a spectral HU curve 400 is illustrated according to one embodiment. The x-axis represents monochromatic energy level in keV and the y-axis represents the HU. In the illustrated embodiment, the recalibration module 160, recalibrates every voxel of the received monochromatic image to the desired monochromatic energy level based on the spectral HU curve 400. Referring back to FIG. 1, in another embodiment, the recalibration module 160 recalibrates the received monochromatic image based on the MD images and the corresponding noise maps. In such an embodiment, the recalibration module 160 regenerates the MD images and the noise maps based on the desired monochromatic energy level. The recalibration module 160 then recalibrates the received monochromatic image to the desired monochromatic energy level based on the one or more regenerated MD images and the corresponding noise maps.

In either embodiment, the recalibration module 160 is further configured to generate graphical data for providing a user interface including the recalibrated monochromatic image to, for example, an administrator of the system controller 130. In one embodiment, the recalibration module 160 sends the graphical data to a display device (not shown) coupled to the system controller 130. In such an embodiment, the display device (not shown) renders the graphical data and displays the user interface. In another embodiment, recalibration module 160 sends the recalibrated monochromatic image to an administrator of the system controller 130 via, for example, e-mail, short messaging service, a voice message, and the like.

Figure 5:
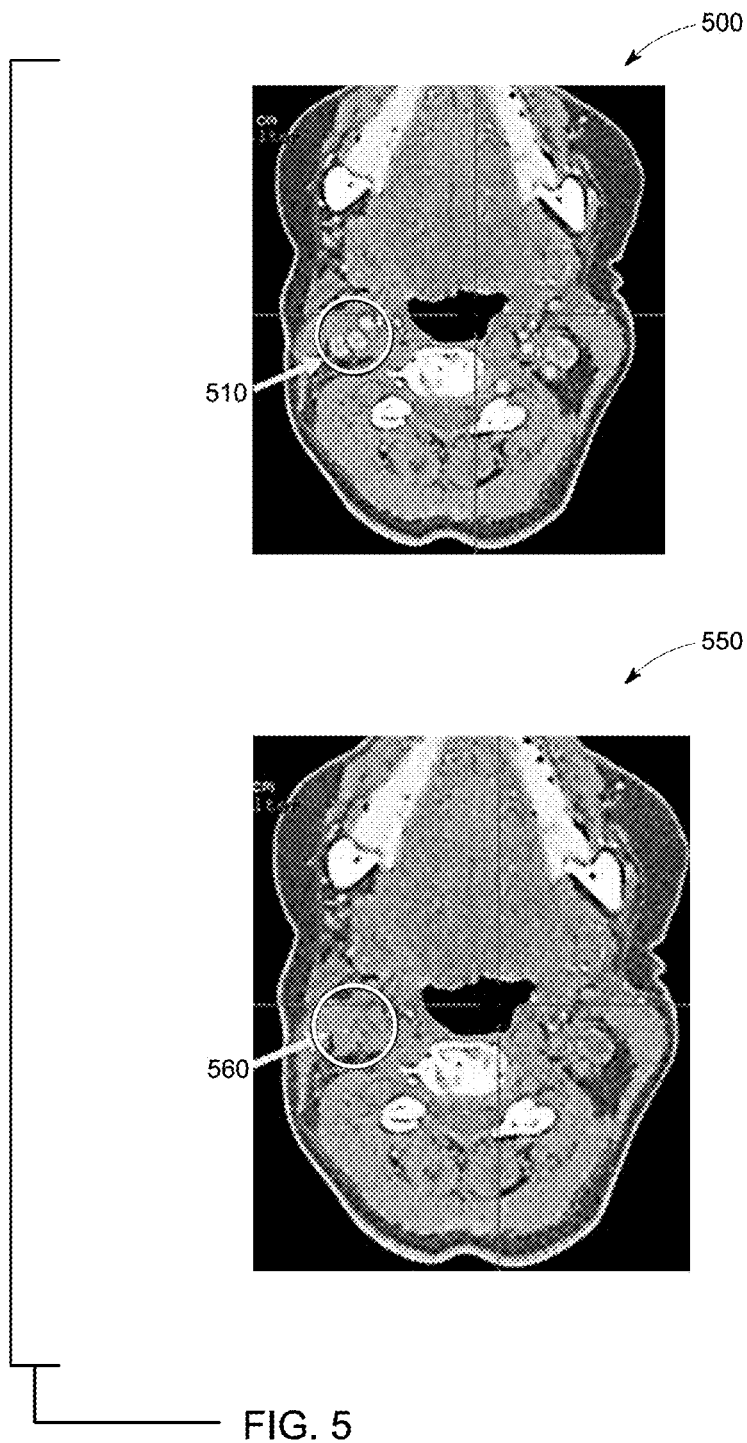
FIG. 5 is a monochromatic image before and after recalibration according to one embodiment.

FIG. 5 illustrates a monochromatic image before 500 and after 550 recalibration according to one embodiment. In the illustrated embodiment, the recalibration sub-system receives the monochromatic image 500 comprising a head of a subject from a CT scanner. The recalibration sub-system detects the petrous bone of the head and computes the monochromatic energy level as 124 keV based on the mass attenuation coefficients of the petrous voxels. The recalibration sub-system determines that the computed monochromatic energy level of the received monochromatic image is different from the desired monochromatic energy level i.e., 140 keV. The recalibration sub-system then recalibrates the monochromatic image 550 to the desired monochromatic energy level.

The intensity levels of the group of voxels 510 in the monochromatic image 500 before recalibration indicate a high contrast region in the head of the subject. If the uncalibrated monochromatic image 500 is used for generating, for example, perfusion or angiography images of the subject, the group of voxels 510 may be erroneously diagnosed as a tumor, a block in a blood vessel, and the like. The recalibration sub-system is more particular since the intensity levels of the corresponding group of voxels 560 in the recalibrated monochromatic image 550 do not indicate the same region in the head as a high contrast region. The petrous bones are the primary ossification centers in the human skull and are known to be the densest regions in the human body with a high level of similarity across a variety of human subjects. Since the recalibration sub-system automatically detects a drift in the energy level and recalibrates the monochromatic image based on the petrous bone, the recalibrated monochromatic image is highly accurate and robust to the variations (e.g., different subjects, switching operations of the X-ray sources, and the like) causing the energy level drift.

Figure 6:
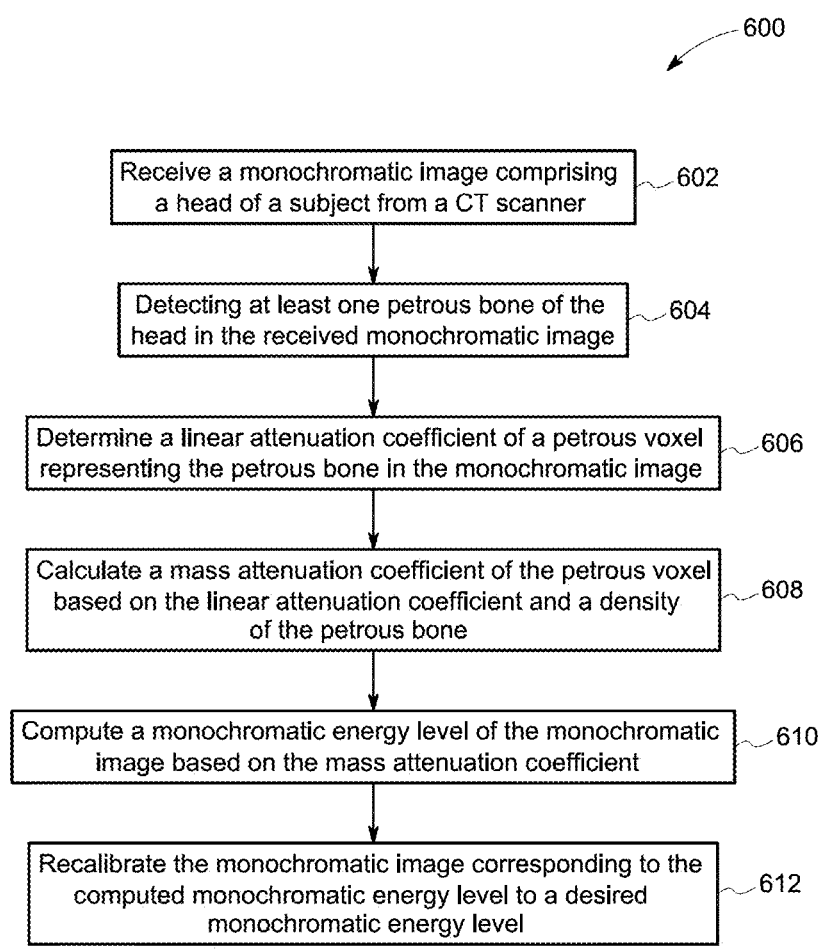
FIG. 6 is a flow diagram illustrating a method for recalibrating a monochromatic image according to one embodiment.

FIG. 6 is a flow diagram illustrating a method 600 for recalibrating a monochromatic image according to one embodiment. The communication unit receives a monochromatic image comprising a head of a subject from a CT scanner 602. The petrous detector detects at least one petrous bone of the head in the monochromatic image 604. For example, the petrous detector determines a petrous bone based on the attenuation values of each voxel in the received monochromatic image. The attenuation unit determines a linear attenuation coefficient of a petrous voxel representing the petrous bone in the monochromatic image 606. The attenuation unit then calculates a mass attenuation coefficient of the petrous voxel based on the linear attenuation coefficient and a density of the petrous bone 608. The attenuation unit also computes a monochromatic energy level of the monochromatic image based on the mass attenuation coefficient 610. The recalibration module recalibrates the monochromatic image corresponding to the computed monochromatic energy level to a desired monochromatic energy level 612. For example, the recalibration module recalibrates the received monochromatic image based on a spectral HU curve in response to determining that the computed monochromatic energy level is different from the desired monochromatic energy level. The recalibration module receives the desired monochromatic energy level from, for example, an administrator of the system controller.

It is to be understood that not necessarily all such objects or advantages described above may be achieved in accordance with any particular implementation. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the technology has been described in detail in connection with only a limited number of implementations, it should be readily understood that the invention is not limited to such disclosed implementations. Rather, the technology can be modified to incorporate any number of variations, alterations, substitutions or equivalent arrangements not heretofore described, but which are commensurate with the spirit and scope of the disclosure. Additionally, while various implementations of the technology have been described, it is to be understood that aspects of the technology may include only some of the described implementations. Accordingly, the inventions are not to be seen as limited by the foregoing description, but are only limited by the scope of the appended claims.

What is claimed is:

1. A method for recalibrating a monochromatic image, the method comprising:
   receiving a monochromatic image comprising a head of a subject from a computed tomography (CT) scanner;
   detecting a petrous bone of the head in the monochromatic image;
   determining a linear attenuation coefficient of at least one petrous voxel representing the petrous bone;
   calculating a mass attenuation coefficient of the petrous voxel based on the linear attenuation coefficient and a density of the petrous bone;
   computing a monochromatic energy level of the monochromatic image based on the mass attenuation coefficient of the petrous voxel; and
   recalibrating the monochromatic image corresponding to the computed monochromatic energy level to the desired monochromatic energy level.

2. The method of claim 1, wherein detecting the petrous bone further comprises:
   determining whether an attenuation value of one or more voxels of the monochromatic image exceeds a petrous threshold value; and
   detecting the one or more voxels as the petrous bone in response to determining that the attenuation value of the one or more voxels exceeds the petrous threshold value.

3. The method of claim 2, further comprising detecting the one or more voxels as the petrous bone based on positional information of the one or more voxels in the monochromatic image.

4. The method of claim 1, wherein recalibrating the monochromatic image further comprises:
   regenerating one or more material decomposition images based on the desired monochromatic energy level; and
   recalibrating the monochromtic image corresponding to the computed monochromatic energy level to the desired monochromatic energy level based on the one or more regenerated material decomposition images.

5. The method of claim 1, further comprising recalibrating the monochromatic image corresponding to the computed monochromatic energy level to the desired monochromatic energy level based on a spectral Hounsfield Unit curve.

6. A system for recalibrating a monochromatic image, the system comprising:
   at least one processor;
   a petrous detector stored in a memory and executable by the at least one processor, the petrous detector configured to receive the monochromatic image comprising a head of a subject from a computed tomography (CT) scanner and detect a petrous bone of the head in the CT image;
   an attenuation unit stored in the memory and executable by the at least one processor, the attenuation unit communicatively coupled with the petrous detector and configured to determine a linear attenuation coefficient of at least one petrous voxel representing the petrous bone, calculate a mass attenuation coefficient of the petrous voxel based on the linear attenuation coefficient and a density of the petrous bone and compute a monochromatic energy level of the monochromatic image based on the mass attenuation coefficient of the petrous voxel; and a recalibration module stored in the memory and executable by the at least one processor, the recalibration module communicatively coupled with the attenuation unit and configured to recalibrate the monochromatic image corresponding to the computed monochromatic energy level to the desired monochromatic energy level.

7. The system of claim 6, wherein the petrous detector is further configured to determine whether an attenuation value of one or more voxels in the monochromatic image exceeds a petrous threshold value and detect the one or more voxels as the petrous bone in response to determining that the attenuation value of the one or more voxels exceeds the petrous threshold value.

8. The system of claim 7, wherein the petrous detector is further configured to detect the one or more voxels as the petrous bone based on positional information of the one or more voxels in the monochromatic image.

9. The system of claim 6, wherein the recalibration module is further configured to regenerate one or more material decomposition images based on the desired monochromatic energy level and recalibrate the monochromatic image corresponding to the computed monochromatic energy level to the desired monochromatic energy level based on the one or more regenerated material decomposition images.

10. The system of claim 6, wherein the recalibration module is further configured to recalibrate the monochromatic image corresponding to the computed monochromatic energy level to the desired monochromatic energy level based on a spectral Hounsfield Unit curve.

* * * * *